US006174708B1

(12) United States Patent
Sodoyer et al.

(10) Patent No.: US 6,174,708 B1
(45) Date of Patent: Jan. 16, 2001

(54) PREPARATION OF A MULTICOMBINATORIAL LIBRARY OF ANTIBODY GENE EXPRESSION VECTORS

(75) Inventors: Regis Sodoyer, Saint Foy les Lyon; Luc Aujame, Fleurieux sur l'Arbresle; Frédérique Geoffroy, Bessenay; Annabelle Bouchardon, Lyons, all of (FR)

(73) Assignee: Pasteur Merieux Serums & Vaccins, Lyon Cedex (FR)

( * ) Notice: Under 35 U.S.C. 154(b), the term of this patent shall be extended for 0 days.

(21) Appl. No.: 09/101,629

(22) PCT Filed: Dec. 4, 1996

(86) PCT No.: PCT/FR96/01938

§ 371 Date: Jan. 22, 1999

§ 102(e) Date: Jan. 22, 1999

(87) PCT Pub. No.: WO97/20923

PCT Pub. Date: Jun. 12, 1997

(30) Foreign Application Priority Data

Dec. 4, 1995 (FR) .................................................. 95 14325

(51) Int. Cl.[7] .............................. C12P 19/34; C12N 15/63
(52) U.S. Cl. ......................... 435/91.1; 435/477; 435/488
(58) Field of Search ................................. 435/91.1, 91.5, 435/471, 475, 477, 488

(56) References Cited

FOREIGN PATENT DOCUMENTS

| WO 92/20791 | 11/1992 | (WO) . |
| WO 93/19172 | 9/1993 | (WO) . |
| WO 95/21914 | 8/1995 | (WO) . |
| WO 96/07754 | 3/1996 | (WO) . |

OTHER PUBLICATIONS

Backman et al. "Use of Synchronous Site–Specific Recombination In Vivo to Regulate Gene Expression." *Bio/Technology.* Dec. 1984, pp. 1045–1049.

Waterhouse et al. "Combinatorial Infection and In Vivo Recombination: A Strategy for Making Large Phage Antibody Repertoires." *Nucleic Acids Research,* 1993, vol. 21, No. 9, pp. 2265–2266.

Geoffroy, F. et al., "A new phage display system to construct multicombinatorial libraries of very large antibody repertoires", 1994, Gene, vol. 151, No. 1–2, pp. 109–113.

Sodoyer, R. et al., "A new phage display system to construct multicombinatorial libraries of very large antibody repertoires", 1995, 9th International Congress of Immunology, vol. 0, No. 0, p. 464.

Nunes–Duby, S.E. et al., "Half–att site substrate reveal the homology independence and minimal protein requirements for productive synapis in Lambda excisive recombination", 1989, Cell, vol. 59, No. 1, pp. 197–206.

Segall, A.M. and Nash, H.A., Synaptic intermediates in bacteriophage lambda site–specific recombination: integrase can align pairs of attachment sites, 1993, Embo Journal, vol. 12, No. 12, pp. 4567–4576.

Kim, S. and Landy, A., "Lambda Int protein bridges between higher order complexes at two distant chromosomal loci attL and attR", 1992, Science, vol. 256, No. 5054, pp. 198–203.

*Primary Examiner*—Robert A. Schwartzman
(74) *Attorney, Agent, or Firm*—McDonnell Boehnen Hulbert & Berghoff

(57) ABSTRACT

On the basis of a first repertoire of genes coding for a population of one of two kinds of polypeptides capable of being optionally covalently combined, particularly variable regions of either the antibody light chain type or the antibody heavy chain type, and at least one gene coding for the other type of polypeptide, particularly a variable region of the other type, an antibody chain or preferably a second repertoire of genes coding for a population of said other type, the genes from the first repertoire are inserted into a first vector to form a population of vectors carrying the various genes of said first repertoire, and said gene of said other type or the genes from said second repertoire is/are inserted into a second vector. Both starting vectors have means enabling each to exchange one part by one or more irreversible recombinations to generate recombinant final vectors of which one contains a gene of one of said types and a gene of the other type.

25 Claims, 2 Drawing Sheets

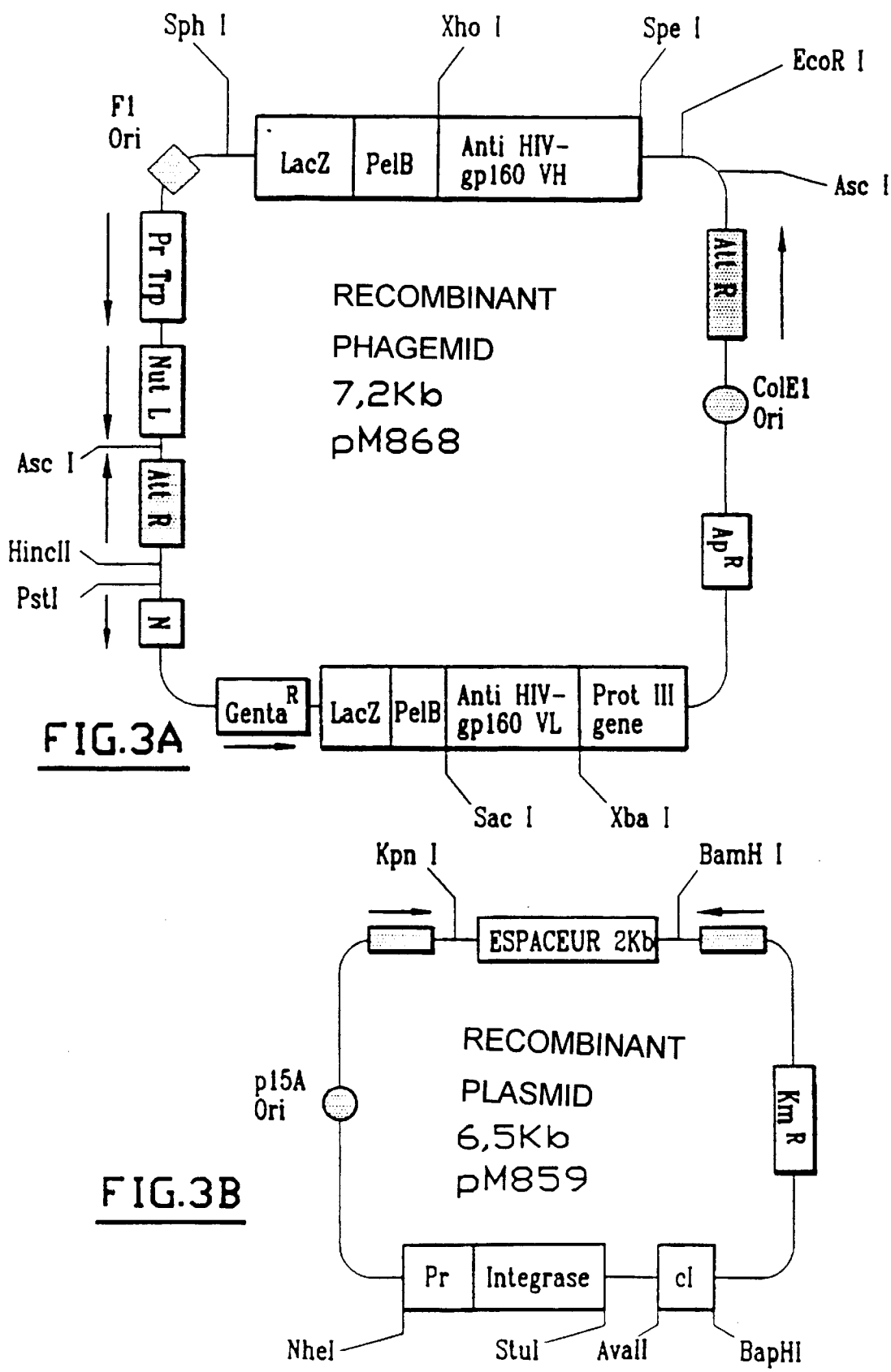

SEQUENCE LISTING

<160> NUMBER OF SEQ ID NOS: 36

<210> SEQ ID NO 1
<211> LENGTH: 36

```
<212> TYPE: DNA
<213> ORGANISM: Artificial Sequence
<220> FEATURE:
<223> OTHER INFORMATION: Description of Artificial Sequence: AttP
      Eco-Nhe+ primer

<400> SEQUENCE: 1
ggaattccgg ctagccgcgc taatgctctg ttacag                           36

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: AttP Kpn-
      primer

<400> SEQUENCE: 2
ggggtacccc atcaaataat gattttattt                                  30

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: AttP
      Xba-Nhe+ primer

<400> SEQUENCE: 3
gctctagagg gctagcgcta atgctctctg ttacag                           36

<210> SEQ ID NO 4
<211> LENGTH: 29
<212> TYPE: DNA
<213> ORGANISM: Artificial Sequence
<220> FEATURE:
<223> OTHER INFORMATION: Description of Artificial Sequence: AttP Bam-
      primer

<400> SEQUENCE: 4
cgggatccca tcaaataatg attttattt                                   29

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Genta 3'
      primer

<400> SEQUENCE: 5
ttggcgcgcc gaattgttag gtggcggtac ttg                              33

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence:
      AttP-Genta 5'primer

<400> SEQUENCE: 6
aaaatcatta tttgatggga tcctaagcct gttcggttcg taaac                 45

<210> SEQ ID NO 7
<211> LENGTH: 26
<212> TYPE: DNA
```

```
<213> ORGANISM: Artificial Sequence
<220> FEATURE:
<223> OTHER INFORMATION: Description of Artificial Sequence: AttB Sph+
      primer

<400> SEQUENCE: 7 cctgctttt tatactaact tgcatg                                            26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: AttB Sph-
      primer

<400> SEQUENCE: 8
caagttagta taaaaaagca ggcatg                                            26

<210> SEQ ID NO 9
<211> LENGTH: 55
<212> TYPE: DNA
<213> ORGANISM: Artificial Sequence
<220> FEATURE:
<223> OTHER INFORMATION: Description of Artificial Sequence: pM851 AscI+
      primer

<400> SEQUENCE: 9
ttggcgcgcc ccaagttagt ataaaaaagc aggcagctcg aactccccTt aataa            55

<210> SEQ ID NO 10
<211> LENGTH: 53
<212> TYPE: DNA
<213> ORGANISM: Artificial Sequence
<220> FEATURE:
<223> OTHER INFORMATION: Description of Artificial Sequence: pM851 AscI-
      primer

<400> SEQUENCE: 10
ttggcgcgcc caagttagta taaaaaagca gcctgccgac ttccattcaa caa              53

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Seq pac-
      primer

<400> SEQUENCE: 11
gttttcagag caagaga                                                      17

<210> SEQ ID NO 12
<211> LENGTH: 21
<212> TYPE: DNA
<213> ORGANISM: Artificial Sequence
<220> FEATURE:
<223> OTHER INFORMATION: Description of Artificial Sequence: Oligo mut
      Xho primer

<400> SEQUENCE: 12
atcgcggcct tgagcaagac g                                                 21

<210> SEQ ID NO 13
<211> LENGTH: 36
<212> TYPE: DNA
<213> ORGANISM: Artificial Sequence
```

<220> FEATURE:
<223> OTHER INFORMATION: Description of Artificial Sequence: Poly1
      primer

<400> SEQUENCE: 13
cgcgcctcta gacgccatgg gcatgcgcga attcgg                                    36

<210> SEQ ID NO 14
<211> LENGTH: 36
<212> TYPE: DNA
<213> ORGANISM: Artificial Sequence
<220> FEATURE:
<223> OTHER INFORMATION: Description of Artificial Sequence: Poly2
      primer

<400> SEQUENCE: 14
cgcgccgaat tcgcgcatgc ccatggcgtc tagagg                                    36

<210> SEQ ID NO 15
<211> LENGTH: 44
<212> TYPE: DNA
<213> ORGANISM: Artificial Sequence
<220> FEATURE:
<223> OTHER INFORMATION: Description of Artificial Sequence: Genta 5'
      primer

<400> SEQUENCE: 15
ttggcgcgcc aggagctatg gagcagcaac gatgttacgc agca                           44

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence: ColE1 Mlu+
      primer

<400> SEQUENCE: 16
ttcgacgcgt ctgtcagacc aagtttactc                                           30

<210> SEQ ID NO 17
<211> LENGTH: 27
<212> TYPE: DNA
<213> ORGANISM: Artificial Sequence
<220> FEATURE:
<223> OTHER INFORMATION: Description of Artificial Sequence: ColE1 Bam-
      primer

<400> SEQUENCE: 17
cgggatcctc ttccgcttcc tcgctca                                              27

<210> SEQ ID NO 18
<211> LENGTH: 27
<212> TYPE: DNA
<213> ORGANISM: Artificial Sequence
<220> FEATURE:
<223> OTHER INFORMATION: Description of Artificial Sequence: AttB Bam+
      primer

<400> SEQUENCE: 18
cgggatccgg aattcgagct gcctgct                                              27

<210> SEQ ID NO 19
<211> LENGTH: 30
<212> TYPE: DNA
<213> ORGANISM: Artificial Sequence
<220> FEATURE:

<223> OTHER INFORMATION: Description of Artificial Sequence: Kan Mlu-
      primer

<400> SEQUENCE: 19
ttcgacgcgt aggcctgaat cgccccatca                                         30

<210> SEQ ID NO 20
<211> LENGTH: 25
<212> TYPE: DNA
<213> ORGANISM: Artificial Sequence
<220> FEATURE:
<223> OTHER INFORMATION: Description of Artificial Sequence: GeneIII
      Xba+ primer

<400> SEQUENCE: 20
gctctagagt ggtggcggtg gctct                                              25

<210> SEQ ID NO 21
<211> LENGTH: 30
<212> TYPE: DNA
<213> ORGANISM: Artificial Sequence
<220> FEATURE:
<223> OTHER INFORMATION: Description of Artificial Sequence: GeneIII
      Sph-primer

<400> SEQUENCE: 21
acacatgcat gcttaagact ccttattacg                                         30

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence: 5'N NluI
      primer

<400> SEQUENCE: 22
ttcgacgcgt aagtgcgatt ccggattagc                                         30

<210> SEQ ID NO 23
<211> LENGTH: 27
<212> TYPE: DNA
<213> ORGANISM: Artificial Sequence
<220> FEATURE:
<223> OTHER INFORMATION: Description of Artificial Sequence: 3'N BglII
      primer

<400> SEQUENCE: 23
gaagatctaa tatctaagta actagat                                            27

<210> SEQ ID NO 24
<211> LENGTH: 49
<212> TYPE: DNA
<213> ORGANISM: Artificial Sequence
<220> FEATURE:
<223> OTHER INFORMATION: Description of Artificial Sequence: N Genta 5'
      BglII primer

<400> SEQUENCE: 24
atctagttac ttagatatta gatcttcaga gctatggagc agcaacgat                    49

<210> SEQ ID NO 25
<211> LENGTH: 69
<212> TYPE: DNA
<213> ORGANISM: Artificial Sequence
<220> FEATURE:
<223> OTHER INFORMATION: Description of Artificial Sequence: nutL1

-continued primer

<400> SEQUENCE: 25
ggccgcacat cagcaggacg cactgaccac catgaaggtg acgctcttaa aaattaagcc    60
ctgaagaag    69

<210> SEQ ID NO 26
<211> LENGTH: 65
<212> TYPE: DNA
<213> ORGANISM: Artificial Sequence
<220> FEATURE:
<223> OTHER INFORMATION: Description of Artificial Sequence: nutL2
     primer

<400> SEQUENCE: 26
cttcttcagg gcttaatttt taagagcgtc accttcatcg tggtcagtgc gtcctgctga    60
tgtgc    65

<210> SEQ ID NO 27
<211> LENGTH: 55
<212> TYPE: DNA
<213> ORGANISM: Artificial Sequence
<220> FEATURE:
<223> OTHER INFORMATION: Description of Artificial Sequence: nutL3
     primer

<400> SEQUENCE: 27
ggcagcattc aaagcagaag gctttggggt gtgtgatacg aaacgaagca ttggc    55

<210> SEQ ID NO 28
<211> LENGTH: 59
<212> TYPE: DNA
<213> ORGANISM: Artificial Sequence
<220> FEATURE:
<223> OTHER INFORMATION: Description of Artificial Sequence: nutL4
     primer

<400> SEQUENCE: 28
ggccgccaat gcttcgtttc gtatcacaca ccccaaagcc ttctgctttg aatgctgcc    59

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence: P15A Xb+
     primer

<400> SEQUENCE: 29
aatctagagg agtgtatact ggctaa    26

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence: P15A Sph-
     primer

<400> SEQUENCE: 30
aggcgcatgc ttaataagat gatcttcttg    30

<210> SEQ ID NO 31
<211> LENGTH: 29
<212> TYPE: DNA

-continued

```
<213> ORGANISM: Artificial Sequence
<220> FEATURE:
<223> OTHER INFORMATION: Description of Artificial Sequence: Pro Lac
      Sph+primer

<400> SEQUENCE: 31
acacatgcat gcgcccaata cgcaaaccg                                    29

<210> SEQ ID NO 32
<211> LENGTH: 26
<212> TYPE: DNA
<213> ORGANISM: Artificial Sequence
<220> FEATURE:
<223> OTHER INFORMATION: Description of Artificial Sequence: Amp Xba-
      primer

<400> SEQUENCE: 32
gctctagatt accaatgctt aatcag                                       26

<210> SEQ ID NO 33
<211> LENGTH: 33
<212> TYPE: DNA
<213> ORGANISM: Artificial Sequence
<220> FEATURE:
<223> OTHER INFORMATION: Description of Artificial Sequence: Amb PCR
      primer

<400> SEQUENCE: 33
gctctagact aactagtttt gtcacaagat ttg                               33

<210> SEQ ID NO 34
<211> LENGTH: 34
<212> TYPE: DNA
<213> ORGANISM: Artificial Sequence
<220> FEATURE:
<223> OTHER INFORMATION: Description of Artificial Sequence: AttP
      Eco/Spe-primer

<400> SEQUENCE: 34
ggactagtta agaattcatc aaataatgat ttta                              34

<210> SEQ ID NO 35
<211> LENGTH: 43
<212> TYPE: DNA
<213> ORGANISM: Artificial Sequence
<220> FEATURE:
<223> OTHER INFORMATION: Description of Artificial Sequence: Pro Trp Mut
      Kpn+primer

<400> SEQUENCE: 35
cggggtacca caattaatca tcgaacaagt tatctagtac gca                    43

<210> SEQ ID NO 36
<211> LENGTH: 26
<212> TYPE: DNA
<213> ORGANISM: Artificial Sequence
<220> FEATURE:
<223> OTHER INFORMATION: Description of Artificial Sequence: Pro Trp
      Kpn-primer

<400> SEQUENCE: 36
ggggtacctt taaagtcggt ttttgt                                       26
```

PREPARATION OF A MULTICOMBINATORIAL LIBRARY OF ANTIBODY GENE EXPRESSION VECTORS

Antibody molecules are constituted by a combination of two heavy chains (H) and two light chains (L) connected by disulphide bridges. The two heavy chains are joined together in a Y shaped structure and the two light chains are respectively bonded to the two branches of that structure, so that the variable regions of the light chains ($V_L$) and heavy chains ($V_H$) are located next to each other. Binding to an antigen results from the properties of the variable portions of the light and heavy chains. A complex rearrangement and selection system can rapidly induce a large quantity of antibodies specifically directed against an antigen.

The conventional hybridoma technique can be used to select clones of hybrid cells expressing genes coding for the light and heavy chains of an antibody molecule. This technique necessitates the fusion of cells of lymphocytic origin, containing the genes for antibody formation and cells forming immortal lines. The cells carrying the genes in question are generally obtained by random creation of libraries of circulating cells with or without prior immunisation with the specific antigen, and screening of the hybridomas by means of an antigen-antibody reaction after multiplication and culture of the hybridoma clones. This technique is difficult, the yield is limited, and screening is not easy.

A further method using recombinant bacteriophages has recently been used. The principles and the various implementations of that method have been described, for example, by D. R. Burton, Tiptech—May 1991, vol. 9, 169–175; D. J. Chiswell et al., Tiptech—March 1992, vol. 10, 80–84; H. R. Hoogenboom et al., Rev. Fr. Transfus. Hémobiol., 1993, 36, 19–47 (see also International patent applications PCT WO 92/01047 and 92/20791).

That technique consists of inserting a repertoire of genes for variable antibody regions in association with a bacteriophage gene into a vector under conditions which enable expression of the gene in the form of a fusion protein at the phage surface, exposing the variable regions of the light and heavy chains bonded by their disulphide bridges in the manner of a Fab antibody fragment, and directly selecting the phages by a rapid separation method using the immobilised specific antigen, for example by immunoaffinity chromatography. After elution, the selected phages can infect a bacterium and be used for direct production or to repeat the selection cycles. That method is particularly powerful as in theory very large libraries can be created and screening of the library is very fine, efficient and rapid. One phage which is particularly suitable for that method is the filamentous phage fd, into which the fragment coding for one of the heavy and light chains of the antibody can be fused with the gene for the minor surface protein and into which the fragment coding for the other chain can be inserted, so that after infecting the bacteria with the phage, a population of phages is obtained carrying a fusion protein at their surface with the heavy and light chains in a configuration which is capable of recognizing the antigen, and is thus suitable for screening.

In addition to its simplicity, the advantages of that technique are enormous. Combined with prior amplification of the antibody gene library, a phage with a specific antibody fragment can be selected in a very large population of phages, in the order of $10^7$, which means that human antibody genes can be researched without being obliged to immunise the donor first.

Phages which randomly combine a light chain and a heavy chain can be obtained by cleaving followed by re-ligation or from two separate libraries of light chain genes and heavy chain genes.

However, the number of different clones which can be obtained is limited by the selection yield and by the degree of efficiency of the bacterial transformation.

One way of increasing the number of successful associations combining the light chains of a first library with the heavy chains of a second library has been described by P. WATERHOUSE et al., Nucleic Acids Research, 1993, vol. 21, No. 9, 2265–2266. Up to $10^{12}$ clones can be obtained using a system of specific recombination of loxP sites sensitive to the action of Cre recombinase. However, the combination is reversible. Further, there is no control of the action of the recombinase and the recombinant vectors have no selective advantage over other vectors.

Considering the yield of the recombinant phage selection step which in reality retains only a fraction of the phages of interest, it would be desirable to obtain recombinant vector yields which were as high as possible with as few as possible non-recombinant vectors.

In a previous application (WO 95/21914 filed $2^{nd}$ February 1995 with French priority FR 94 01519 of $10^{th}$ February 1994), the inventors of the present invention described a method for the production of multicombinatorial libraries, in particular in the form of phages or phagemids, from two repertoires of genes, one for light chains and the other for heavy chains, to obtain a high number of clones.

That system has improved non-reversibility and selectivity properties since a new selection marker appears after recombination.

The non-reversibility properties are due to the absence of excision means in the vectors and in the host strain. The examples illustrating that application are thus characterised by the absence of the Xis excision protein in the vectors and in the Xis strain.

Further, the stable character of the joining sequences from recombination of specific recombination sites contributes to the non-reversibility of the system.

The present invention aims to improve that method further, in particular to increase its yield, the ease of implementing it and the diversity of the generated clones.

To this end, after two recombination events, the invention exchanges sequences between the two vectors. This exchange gives rise to two recombinant vectors, one with the two transcription units for the heavy and light chains but which is smaller in size than that of a vector which would result from fusion between the two starting vectors. As the final vector is smaller, its replication and packaging are more efficient and production is also improved, thus increasing the final number of clones.

The invention can also considerably broaden the choice of strains which can be used as host cells, in that it is no longer necessary for the strain used to possess the gene for integrase in its genome, that gene currently being carried by one of the two starting vectors and being found in the final vector.

This means that one is no longer restricted to strains with the gene for integrase integrated into their genome and any highly infectious strain producing phages can be selected (TG1, 71–18 or NM522).

Strains 71–18 (Stratagene; Yanisch-Perron, C. et al., (1985) Gene 33, 103–109) and NM522 (New England Biolabs; Woodcock, D. L., et al., (1989) Nucl. Acids Res. 17, 1563–1575) have proved to be particularly good phage producers. They can multiply the number of phages produced by a factor of 10 to 50 with respect to the D1210HP *E. coli* strain produced by Stratagene.

The invention provides a method for the production of multicombinatorial libraries in which, starting from a first repertoire of genes coding for a population of one of two types of polypeptides, which can covalently or otherwise combine, in particular variable regions of one of the antibody light or antibody heavy chains, and at least one gene coding for the other type of polypeptide, in particular a variable region of the other type, an antibody chain or preferably a second repertoire of genes coding for a population of said other type, introducing the genes of said first repertoire into a first starting vector to form a population of final vectors carrying different genes of said first repertoire, and introducing said gene of said other type or genes of said second repertoire into a second starting vector, and recombining said first and second starting vectors under conditions under which one of the vectors will contain, after recombination, one gene for one of the two types and one gene for the other type, and expressing the two genes in the form of associated polypeptides which can appear on the external surface of the product of said vector and remain there, being combined together multimerically or so as to simulate a multimer, characterised in that said first and second vectors include means for exchanging one portion of each by irreversible recombination(s) to generate recombinant final vectors after the recombination(s), one containing a gene of one of the two types and a gene of the other type.

Advantageously, the method of the invention is further characterised in that the starting vectors respectively contain two specific recombination sites of one or two specific recombination systems, in particular attB sites of *E. coli* and attP sites of lambda phage, arranged so as to allow two recombination events under the influence of an associated recombinase or integrase to form two sequences of stable attachment such as attL and attR in each of the final vectors resulting from recombination.

Preferably, the two recombination sites in each of the starting vectors are in the opposite orientation.

In an advantageous variation, the starting vectors respectively contain two attp lambda phage sites and two attB *E. coli* sites.

Preferably, one of the two starting vectors further comprises a sequence coding for a recombinase or an integrase. This advantageous variation means that any strain which is highly infectious and produces a phage, for example TG1, 71–18 or NM522, can be used without having to be limited to strains containing the gene for one or the other of these enzymes in their genome. Strains NM522 and 71–18 have proved to be particularly important in this context. Preferably, the enzyme used to control the recombination step between the starting vectors is an inducible recombinase, in particular a thermo-inducible recombinase.

Advantageously, in the method of the invention, the final recombinant vector obtained from the starting vectors which contains the genes to be expressed is arranged so as to have a selection marker which is initially non-functional and which is rendered functional by recombination. This marker is a gene for antibiotic resistance, for example, in particular a gene from the group formed by genes resistant to tetracyclines, gentamycin, kanamycin and chloramphenicol, with its promoter.

This selection marker preferably comprises a promoter for the gene, the promoter initially being inserted in one of the starting vectors and the marker gene in the other. The selection gene and its promoter can be separated, for example by an antiterminating sequence, in particular the NutL sequence. The starting vectors also contain at least one phage origin of replication or plasmid origin of replication, the origins being arranged so that the final recombinant vectors each contain only one phage and/or plasmid origin of replication.

In the method of the invention, one of the two genes to be expressed is fused to a sequence coding for all or part of a polypeptide of the phage capsid. This sequence corresponds, for example, to the gene coding for protein III of the lambda phage. The gene to be expressed and the sequence to which it is fused are advantageously located in one of the starting vectors so as to be present in the recombinant phagemid product containing the two genes to be expressed.

The invention also provides vectors obtained or obtainable using the above method, in particular plasmid or phagemid vectors which are characterised by the presence of a sequence coding for one of two types of polypeptides which can combine together, in particular a variable portion of the antibody light chain, and a sequence coding for the other of said two types, in particular a variable portion of the antibody heavy chain, said sequences being accompanied, in suitable frames, by elements allowing their expression in a host, said sequences being separated by stable attachment sequences, in particular attR and attL.

These vectors, in particular plasmid type vectors, preferably comprise a functional sequence coding for a recombinase or integrase, and it is particularly advantageous if they also comprise stable attachment sequences separated by a spacer.

The invention also provides multicombinatorial libraries of vectors formed by the vectors of the invention and combining, in a random fashion, a sequence coding for one of two types of polypeptides which can associate together, in particular a variable portion of the antibody light chain and a sequence coding for the other of said two types, in particular a variable portion of the antibody heavy chain.

Finally, the invention provides antibodies or antibody Fab type portions obtainable after selecting libraries of vectors in accordance with the invention using selection markers, then screening to select the clones expressing associations of the antibody light and heavy chains with the desired affinities for set antigens, then expressing the screened clones in an expression system, and finally extracting and/or purifying the antibodies or antibody Fab type portions produced in the expression system. Selection and screening techniques are described, for example, in Parmley SF et al., Gene 73 (1988), 305–318. Extraction and purification techniques are described, for example, in Neu H. C. et al., (1965), J. Biol. Chem. 240, 3685–3692.

An example will now be given of the construction of a recombinant vector of the invention combining the variable portions of the light chain and the heavy chain of an HIV anti-gp160 clone, a vector which has proved to be capable of expressing genes of said variable light and heavy portions and displaying their expression products on its surface or, in a variation, secreting them in the form of a heavy chain— light chain combination recognizing the gp160 antigen.

The same technique can be used to produce multicombinatorial constructions combining the genes of a repertoire of variable light chain portions with a gene for a variable heavy chain portion or a repertoire of variable heavy chain portions with a gene for the variable light chain portion or two repertoires of variable heavy and light portions.

FIGURES

FIG. 3A–3B is a schematic diagram of the recombinant vectors obtained after sequence exchange between plasmid pM858 and phagemid pM867.

FIG. 3A is the multicombinatorial 7.2 kb phagemid with two transcription units for the heavy and light chains.

FIG. 3B is the 6.5 kb recombinant plasmid containing the integrase gene.

DESCRIPTION OF VECTORS

Figure 1:
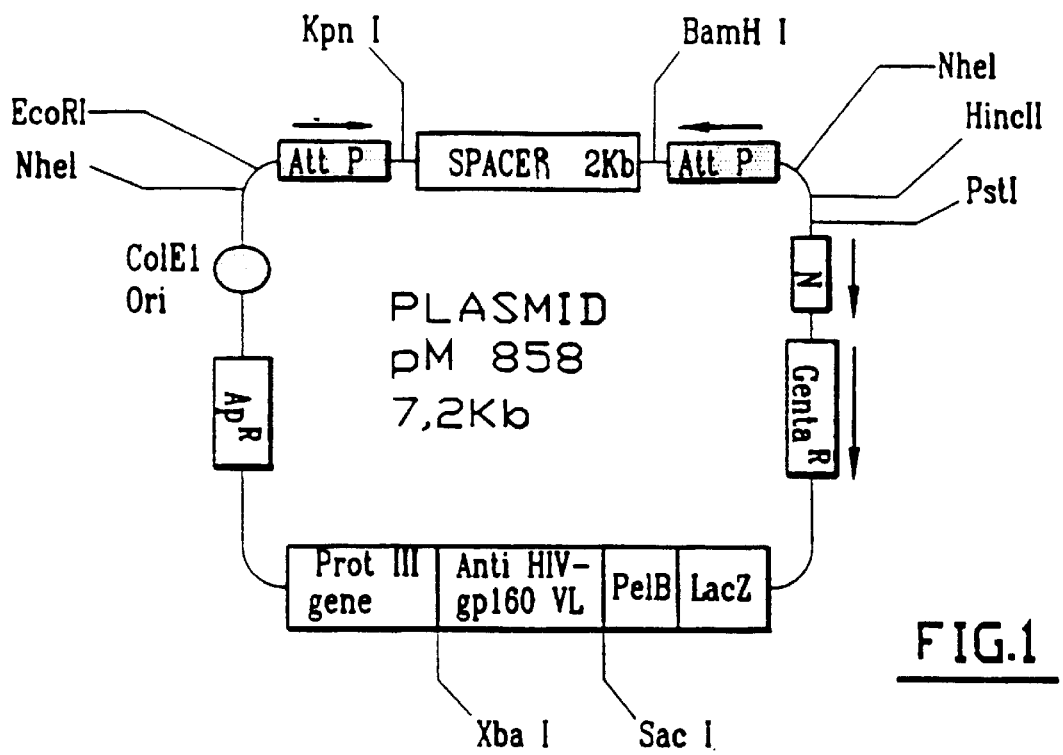
FIG. 1 is a schematic diagram of plasmid pM858 with a transcription unit for the variable light chain regions fused with the gene III.
Figure 2:
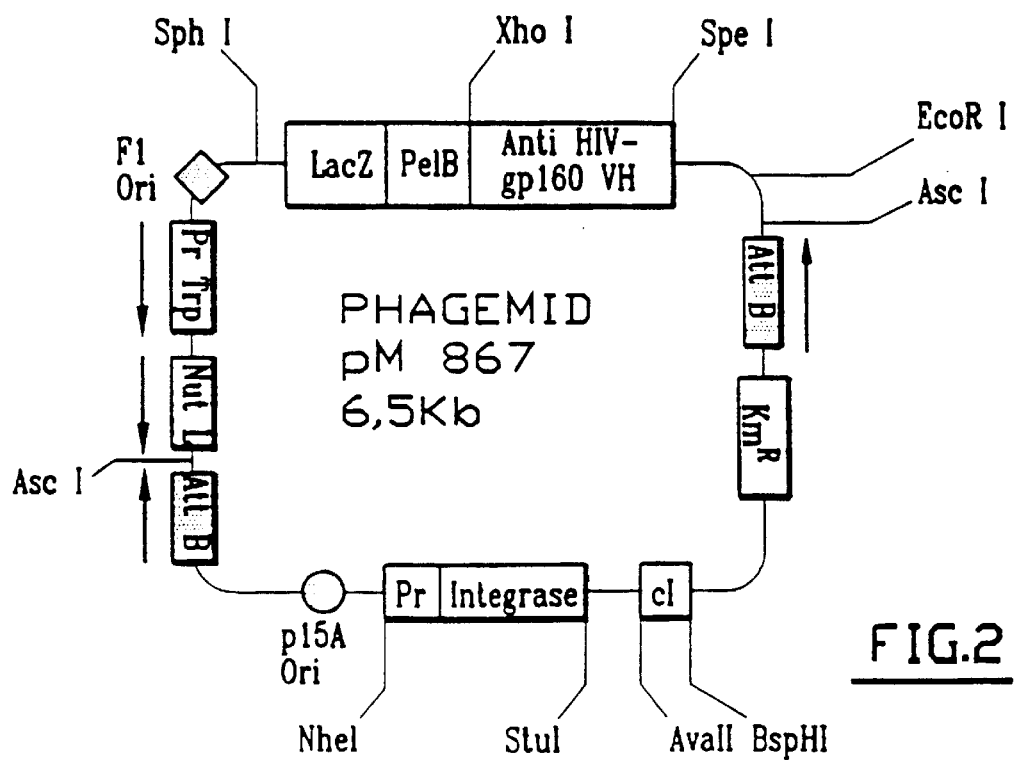
FIG. 2 is a schematic diagram of phagemid pM867 with a transcription unit for the variable heavy chain regions.

Reference should be made to International patent application WO 95/21914, hereby incorporated by reference, for details of the molecular biological techniques used in constructing the vectors.

Plasmid pM858 (7.2 kb): Plasmid with a "high-copy-number" ColE1 origin of replication, a transcription unit for the variable regions of the light chains fused with gene III (lacZ promoter—PelB signal sequence-VH gene III), gene N followed by the gene coding for the gentamycin selection marker, the ampicillin selection marker and two attP recombination sequences in the opposite orientation separated by a spacer which must be at least 2 kb.

Phagemid pM867 (6.5 kb): Vector with a "low-copy-number" origin of replication p15A, lambda phage integrase and the heat sensitive repressor cI857, a kanamycin selection marker, and two attB recombination sequences in the opposite orientation separated by the following sequences: one transcription unit for the variable heavy chain regions (lacZ-pelB-VH), the origin of replication for phage F1, the tryptophane promoter Trp followed by the antiterminator NutL in the same orientation.

After recombination (2 recombination events), the sequences separating the recombination sequences had been exchanged between the starting phagemid and the plasmid. A recombinant phagemid was obtained with two attR sequences in the opposite orientation separated by elements from the starting plasmid, namely the unit for transcription of the variable heavy chain regions, the F1 origin, the Trp promoter followed by NutL. In the recombinant phagemid containing two transcription units for the heavy and light chains, a transcription unit for a new selection marker, in this case gentamycin (Trp promoter-NuTL-N-gentamycin) was also created.

The other properties of this system (non-reversibility, new selection marker after recombination) were identical to that of the prior art system described in WO 95/21914.

I—Description of the various steps of constructing the two starting vectors.

I. Creation of a plasmid with an origin of replication ColE1, an ampicillin resistance gene, a gentamycin resistance gene (without its promoter), the N protein gene, the cassette for cloning the light chains and 2 attP recombination sequences framing a spacer of about 2 kb.

This vector acted as a starting point for insertion of the library of light chains (variable regions).

1. Insertion of first recombination sequence attP (271 bp) after PCR amplification on λ phage (bases 27571 to 27820), between the EcoRI and KpnI sites of pUC18 plasmid (2686 bp) (controlled orientation).

Plasmid pM852 was obtained (2957 bp).

```
AttP Eco-Nhe+ primer:                    (SEQ ID NO.:1)
5' GGAATTCCGGCTAGCCGCGCTAATGCTCTGTTACAG3'
     EcoRI    SphI AttP Kpn- primer:                        (SEQ ID NO.:2)
5' GGGGTACCCCATCAAATAATGATTTTATTT 3'
     KpnI
```

2. Insertion of gentamycin resistance gene (gene aacC1) coupled to the second recombination sequence attP.

The attP sequence was amplified by PCR of the λ phage from bases 27571 to 27820 using the following primers:

```
AttP Xba-Nhe+ primer:                    (SEQ ID NO.:3)
5' GCTCTAGAGGGCTAGCGCTAATGCTCTCTGTTACAG 3'
     XbaI    NheI AttP Bam- primer:                        (SEQ ID NO.:4)
5' CGGGATCCCATCAAATAATGATTTTATTT 3'
     BamHI
```

The aacc1 gene of 732 bp was amplified from plasmid pSS11 9 (ref: STIBITZ. S., Methods in enzymology Vol 235, 458–465, 1994).

```
Genta 3' primer:                         (SEQ ID NO.:5)
5' TTGGCGCGCCGAATTGTTAGGTGGCGGTACTTG 3'
     AscI AttP-Genta5' primer:                     (SEQ ID NO.:6)
5' AAAATCATTATTTGATGGGATCCTAAGCCTGTTCGGTTCG-
TAAAC 3'
```

A second PCR amplification reunited the above two sequences using the following primers:

```
AttP Xba-Nhe+ primer:                    (SEQ ID NO.:3)
5' GCTCTAGAGGGCTAGCGCTAATGCTCTCTGTTACAG 3'
     XbaI    NheI Genta 3' primer:                         (SEQ ID NO.:5)
5' TTGGCGCGCCGAATTGTTAGGTGGCGGTACTTG 3'
     AscI
```

The fragment comprising the aacc1 gene and the attP sequence digested with XbaI was cloned in the pM852 vector at sites SmaI and XbaI with destruction of the SmaI site (controlled orientation).

Plasmid pM854 was obtained (3960 bp).

3. Deletion of a portion of the sequence framing the β-galactosidase gene in plasmid pM854 by digestion with HindIII and SspI, then treating the extremities of the vector with Klenow polymerase and ligating the plasmid to itself with destruction of the two restriction sites.

Plasmid pM855 was obtained (3378 bp).

4. The restriction site XbaI was destroyed by digesting vector pM855 with Xba1 and treating the extremities with Klenow.

Plasmid pM856 was obtained (3382 bp).

5. Insertion of an expression cassette for the light chain (lac promoter, PelB signal sequence and light chain (642 bp) of an HIV anti-gp 160 clone fused to gene III) coupled to a system supplying a new resistance to the recombined phagemid (gene for N protein and aacc1 gene depleted of its promoter).

The complete fragment (2609 bp) was obtained from plasmid pM845 (described below) by complete digestion with SphI and partial digestion with Asp718. The fragment after treating its extremities with Klenow was cloned in plasmid pM856 cut with SphI and also treated with Klenow, with destruction of the phI site.

Plasmid pM857 was obtained (5991 bp).

6. Plasmid pM857 was deleted from the aacc1 gene by KpnI-BamHI cutting (768 bp) then its extremities were treated with Klenow. A spacer of about 2 Kb will be inserted between the two sites. The sequence of this spacer is still to be determined.

Plasmid pM858 was obtained (about 7200 bp).

II. Creation of a phagemid type vector carrying two origins of replication P15A and f1, a kanamycin resistance gene, two attB recombination sequences framing the heavy chain cloning cassette, the tryptophane promoter and the nutL sequence.

This vector acted as the starting point for inserting a library of heavy chains (variable regions).

The base plasmid for the construction was plasmid pM825 (described in application WO 95/21914).

1. Insertion of a second attB recombination sequence of 23 bp in the form of synthetic oligonucleotides into the SphI site. Two possible cloning orientations were obtained. The orientation of interest to us was that of two attB in opposite directions.

Plasmid pM851 was obtained (3079 bp). AttB Sph+ primer: 5' CCTGCTTTTTTATACTAACTTGCATG 3' (SEQ ID NO.: 7) AttB Sph−primer: 3' GTACGGAC-GAAAAAATATGATTGAAC 5' (SEQ ID NO.: 8 )

2. A 2118 bp fragment (covering bases 997 to 3079+0 to 36) of pM851 was amplified by PCR. It comprised the two attB recombination sequences, the gene for kanamycin resistance and the origin of replication P15A with creation of an AscI site at each extremity and elimination of existing EcoRI and SphI sites.

Palasmid pM861 was obtained (2126 bp).

```
pM851 AscI+ primer:
5'TTGGCGCGCCCCAAGTTAGTATAAAAAAGCAGGCAGCTCGAACTCCCCTTAATAA 3'   (SEQ ID NO.:9)
     AscI pM851 AscI- primer:
5'  TTGGCGCGCCCCAAGTTAGTATAAAAAGCAGCCTGCCGACTTCCATTCAACAA 3'    (SEQ ID NO.:10)
     AscI
```

3. Mutagenesis of restriction site XhoI located in position 925 with Clontech kit.

Plasmid pM862 was obtained (2126 bp).

```
Seq pac- primer:                    (SEQ ID NO.:11)
5' GTTTTCAGAGCAAGAGA 3'

Oligo mut Xho primer:               (SEQ ID NO.:12)
5' P-ATCGCGGCCTTGAGCAAGACG 3'
          XhoI destroyed
```

4. Insertion of a synthetic polylinker multiple cloning site of 36 bp comprising sites XbaI, NcoI, SphI, and EcoRI at unique AscI site of vector pM862 (controlled orientation).

Plasmid pM863 was obtained (2162 bp).

```
Poly1 primer:                       (SEQ ID NO.:13)
5' CGCGCCTCTAGACGCCATGGGCATGCGCGAATTCGG 3'

Poly2 primer:                       (SEQ ID NO.:14)
3'     GGAGATCTGCGGTACCCGTACGCGCTTAAGCCGCGC 5'
   AscI  XbaI  NooI  SphI   EcoRI  AmcI
```

5. Insertion of a fragment of 1122 bp comprising the nutL sequence, the tryptophane promoter sequence and the origin of replication f1 into vector pM863. This fragment was extracted from vector pM847 (described below) by digestion with NheI and BspHI, then cloned in vector pM863 at sites XbaI and NcoI (controlled orientation).

Phagemid pM864 was obtained (3284 bp).

6. Insertion of a 1080 bp fragment corresponding to the cassette for expression of heavy chains (lac promoter, PelB signal sequence and heavy chain (684 bp) of an HIV anti-gp160 clone) into vector pM864).

This fragment was extracted from vector pM847 by SphI+EcoRI digestion, then cloned in vector pM864 at SphI and EcoRI sites(controlled orientation).

Phagemid pM865 was obtained (4363 bp).

7. Insertion of the gene for λ integrase and its promoter amplified by PCR (1280 bp) from plasmid pCW107 (Wulfing & Plückthun, Gene 136, 199–203: 1993). This fragment was inserted at sites NheI and StuI of phagemid pM865 (controlled orientation).

Phagemid pM866 was obtained (about 5643 bp).

8. Insertion of the cI857 sequence under the control of λ promoter pR, amplified by PCR (820 bp) from plasmid pCW107. This sequence was required to allow expression of integrase after thermal shock at 42° C. This fragment was inserted at sites AvaII and BspHI of phagemid pM866.

Phagemid pM867 was obtained (about 6463 bp).

The last two steps 7 and 8 can be modified.

The construction of these vectors means that any bacterial strain can be used for recombination (type XL1 blue).

II—Description of plasmids pM845 and pM847 used to construct the starting vectors.

I. Construction of plasmid pM845 with an origin of replication ColE1, a gene for kanamycin resistance, a recombination sequence attB and a cassette for cloning and expression of light chains fused to the product from gene III.

1. Cloning of gene aaсC1 (Gm$^R$) in plasmid pM826.

Amplification by PCR of gene aacC1 (575 bp) free of its promoter, from pSS1129 (Stibitz S., Methods in enzymology, Vol 235, 458–465, 1994) and insertion at the unique AscI site of pM826 described in International application WO 95/21914.

Plasmid pM840 was obtained (3611 bp).

```
Genta 5' primer:                    (SEQ ID NO.:15)
5' TTGGCGCGCCAGGAGCTATGGAGCAGCAACGATGTTACGCAGCA 3'
     AscI Genta 3' primer:                    (SEQ ID NO.:5)
5' TTGGCGCGCCGAATTGTTAGGTGGCGGTACTTG 3'
     AscI
```

2. Change of origin of replication P15A of plasmid pM840 by high-copy-number origin ColE1.

Amplification by PCR of ColE1 (953 bp) from vector pM840 free of origin P15A (2750 bp).

```
ColE1 Mlu+ primer:                  (SEQ ID NO.:16)
```

```
                        -continued
5' TTCGACGCGTCTGTCAGACCAAGTTTACTC 3'
        MluI ColE1 Bam- primer:                      (SEQ ID NO.:17)
5' CGGGATCCTCTTCCGCTTCCTCGCTCA 3'
     BamHI AttB Bam+ primer:                       (SEQ ID NO.:18)
5' CGGGATCCGGAATTCGAGCTGCCTGCT 3'
     BamHI Kan Mlu- primer:                        (SEQ ID NO.:19)
5' TTCGACGCGTAGGCCTGAATCGCCCCATCA 3'
       MluI
```

Assembly of two PCR fragments using newly created MluI and BamHI sites.

Insertion of PCR fragment of 1022 bp at AscI site of pM844 after deleting previously cloned aacC1 gene.

Plasmid pM845 was obtained (4785 bp).

II. Construction of phagemid pM847 with origin of replication P15A, a gene for ampicillin resistance, an attP recombination sequence and a cassette for cloning and expression of heavy chains.

1. Cloning of antiterminator nutL into phagemid pM834 (described in WO 95/21914).

Destruction of NotI site located at 3' of lac promoter by digestion then filling with Klenow.

Synthesis of 4 oligonucleotides covering 120 bp of the nutL sequence of the lambda phage (bases 35467 to 35586) and insertion at NotI site located at 3' of attP recombination sequence. Only one orientation is valid for the antiterminator to function after recombination.

Phagemid pM839 was obtained (4937 bp).

```
Primers nutL1, nutL2, nutL3 and nutL4:
5'                                                                      (SEQ ID NO.:25)
GGCCGCACATCAGCAGGACGCACTGACCACCATGAAGGTGACGCTCTTAAAAATTAAGCCC-
TGAAGAAG 3'                                                                      (SEQ ID NO.:26)
     CGTGTAGTCGTCCTGCGTGACTGGTGCTACTTCCACTGCGAGAATTTTTAATTCGGG-
       NotI
ACTTCTTC GGCAGCATTCAAAGCAGAAGGCTTTGGGGTGTGTGATACGAAACGAAGCATTGGC 3'            (SEQ ID NO.:27)

CCGTCGTAAGTTTCGTCTTCCGAAACCCCACACACTATGCTTTGCTTCGTAACCGCCGG 5'         (SEQ ID NO.:28)
                                                       NotI
```

Plasmid pM842 was obtained (3692 bp).

3. Cloning of gene III at 3' of the light chain in plasmid pM842.

Amplification of gene III by PCR (658 bp) from phagemid pM841 and insertion at 3' of the light chain conserving the reading frame (with an amber codon between the two) between sites XbaI and SphI.

Plasmid pM844 was obtained (4339 bp).

```
GeneIII Xba+ primer:                    (SEQ ID NO.:20)
5' GCTCTAGAGTGGTGGCGGTGGCTCT 3'
      XbaI GeneIII Sph- primer:                    (SEQ ID NO.:21)
5' ACACATGCATGCTTAAGACTCCTTATTACG 3'
        SphI
```

4. Cloning of N protein (necessary for functioning of nutL antiterminator) at 3' of attB and 5' of aacC1 gene.

Amplification of N protein gene by PCR (453 bp) from lambda phage (bases 35022 to 35465) and gene aacC1 (575 bp) from pSS1129 then association of two fragments using a second PCR with 5' N Mlu and Genta 3' primers.

2. Change of origin of replication ColE1 in phagemid pM839 by low-copy-number origin P15A.

Amplification by PCR of P15A (833 bp) from pM840 and vector pM839 free of ColE1 origin (4007 bp).

```
P15A Xb+ primer:                        (SEQ ID NO.:29)
5' AATCTAGAGGAGTGTATACTGGCTAA 3'
      XbaI P15A Sph- primer:                       (SEQ ID NO.:30)
5' AGGCGCATGCTTAATAAGATGATCTTCTTG 3'
       SphI Pro Lac Sph+ primer:                    (SEQ ID NO.:31)
5' ACACATGCATGCGCCCAATACGCAAACCG 3'
         SphI Amp Xba- primer:                        (SEQ ID NO.:32)
5' GCTCTAGATTACCAATGCTTAATCAG 3'
      XbaI
```

Assembly of two PCR fragments using newly created XbaI and SphI sites.

Phagemid pM841 was obtained (4828 bp).

3. Deletion of gene III located at 3' of heavy chain.

```
5'N NluI primer:        5' TTCGACGCGTAAGTGCGATTCCGGATTAGC 3'            (SEQ ID NO.:22)
                                MluI 3'N BglII primer:       5' GAAGATCTAATATCTAAGTAACTAGAT 3'               (SEQ ID NO.:23)
                             BglII N Genta 5' BglII primer: 5' ATCTAGTTACTTAGATATTAGATCTTCAGAGCTATGGAGCAGCAACGAT 3'   (SEQ ID NO.:24)
                                               BglII 3' Genta primer:        5' TTGGCGCGCCGAATTGTTAGGTGGCGGTACTTG 3'         (SEQ ID NO.:5)
                              AscI
```

Amplification by PCR of entire phagemid pM841 but without gene III (4150 bp) and ligation after digestion by the unique site SpeI. Phagemid pM846 was obtained (4144 bp).

```
Amb PCR primer:                           (SEQ ID NO.:33)
5' GCTCTAGACTAACTAGTTTTGTCACAAGATTTG 3'
         SpeI AttP Eco/Spe- primer:                     (SEQ ID NO.:34)
5' GGACTAGTTAAGAATTCATCAAATAATGATTTTA 3'
     SpeI       EcoRI
```

4. Change of cat promoter by trp promoter.

Amplification by PCR of bicistronic tryptophane promoter (233 bp) from vector pM800 (available in the laboratory) and insertion at KpnI site located 3' of the nutL sequence after deleting the previously cloned cat promoter. Phagemid pM847 was obtained (4194 bp).

```
Pro Trp Mut Kpn+ primer:                  (SEQ ID NO.:35)
5' CGGGGTACCACAATTAATCATCGAACAAGTTATCTAGTACGCA 3'
      KpnI Pro Trp Kpn- primer:                      (SEQ ID NO.:36)
5' GGGGTACCTTTAAAGTCGGTTTTTGT 3'
      KpnI
```

III—Recombination between the two vectors pM858 and pM867.

The above two vectors acted as a starting point for the production of libraries of multicombinatorial antibodies. In the example shown recombination occurred between the $V_L$ and $V_H$ chains of the HIV anti-gp160 clones used. However, if the two vectors are constructed from libraries of antibody heavy chain genes and/or light chain genes they can produce a multicombinatorial library of antibodies which can then be screened.

Transformed in a suitable strain (D1210HP), the two vectors can combine because of sequences AttP and AttB, targets for an inducible recombination factor int. The recombination mechanisms are described in Chapter 9 of "The recombination of genetic material" (Miller H. V., Viral and cellular control of site-specific recombination, 1988, p 360–384, edited by Brooks Low K., Academic Press). The multicombinatorial vector (7200 bp) thus created will have an origin of replication, a gene for gentamycin resistance and two cassettes enabling expression of the $V_L$ and $V_H$ chains.

1) Transformation of the *E. coli* XL-1 Blue strain (distributed by Stratagene) by electroporation.
2) Recombination steps.

Transformation of this strain by the pM858 plasmid (containing $V_L$ chains) and transformation of a compatible strain using pM867 phagemid (carrying the $V_H$ chains) were carried out in parallel.

The strain transformed by phagemid pM867 was prepared in the form of a phage then the XL-1 Blue culture containing plasmid pM858 was infected at 30° C. (optical density OD=0.6).

After 30 minutes of infection at 30° C. the culture underwent thermal shock at 42° C. for one hour to initiate recombination under the influence of the inducible recombinase.

After cooling the culture to 30° C. and adding gentamycin the clones were spread on an agar medium containing gentamycin. Helper phage VCSM13 ($Kan^R$) from Stratagene was added in an amount of $10^{12}$ pfu/100 ml of culture. Two hours later 70 µg/ml final of kanamycin was added and the culture was left for a few hours at 30° C.

Analysis of the clones after recombination of vectors pM858 and pM867 showed that combination had occurred. A stable recombinant 7200 bp phagemid was obtained which expressed a Fab and was always capable of infecting the XL-1 Blue strain. The AttL and AttR attachment points were verified by sequencing.

IV—Preparation of a multicombinatorial library of light chains and a library of heavy chains.

Insertion step I.4 of the variable region of the light chain of the HIV anti-gp 160 clone amplified by PCR is replaced by similar insertion of variable light chain regions of a library of antibody light chains amplified by PCR using a known system of primers for the desired type of light chain or by a plurality of primer systems if it is desired to carry out multicombination from populations of different types of light chains. Primer systems enabling light chains to be amplified are well known and described by W. D. Huse et al., Science, vol 246 (1989), 1275–1281.

In the same way, to clone heavy chains step II.1 for insertion of the heavy chain of an HIV anti-gp 160 clone is replaced by inserting a library of variable heavy chain regions amplified by PCR using suitable primer systems described by M. J. Campbell et al., Molecular Immunology Vol. 29, No. 2 (1992), 193–203 or by W. D. Huse et al., cited above.

After the recombination steps, gentamycin-resistant clones are selected and screening is then carried out to select clones expressing combinations of the antibody light chain and antibody heavy chain having the desired affinities for the predetermined antigens, in accordance with techniques described by S. F. Parmley et al., Gene 73, (1988), 305–318.

The clones from the selection and screening steps enable the corresponding Fab molecules to be produced. The phagemid used contains an amber codon at the junction of the heavy Fab chain and gp3. By way of example, when an amber suppressive *E. coli* strain, XL1-Blue (Stratagene, La Jolla, Calif., EU), is transformed with the phagemid, Fab is expressed on the phage surface. In a non-suppressive bacterial strain, for example TOP10 (Stratagene, la Jolla, Calif., EU), the proteic system is interrupted at the extremity of the heavy chain. Because of the signal sequence of the gene coding for the pectase lyase "pelB" of *E. cartovora*, Fab is then transported into the periplasm. It is then extracted by osmotic shock (Neu, H. C. et al., (1965). J. Biol. Chem. 240, 3685–3692). Depending on the nature of the Fab, different known chromatographic techniques can be used to purify it: ion exchange, affinity chromatography, molecular sieve, etc.

What is claimed is:

1. A method for the production of multicombinatorial libraries wherein, (a) a first repertoire of genes coding for a population of one of two types of polypeptides, which can covalently or otherwise combine, and 2) at least one gene coding for the other type of polypeptide or a second repertoire of genes coding for a population of said other type are provided;

(b) the genes of said first repertoire are introduced into a first starting vector to form a population of final vectors carrying different genes of said first repertoire;

(c) said gene of said other type or genes of said second repertoire are introduced into a second starting vector;

(d) and said first and second starting vectors are recombined under conditions under which one of the vectors will contain after recombination one gene for one of the two types and one gene for the other type and the two genes are expressed in the form of associated polypeptides which can be displayed on the surface of said vector and remain there, being combined together multimerically or so as to simulate a multimer; thereby producing a multicombinational library;

said first and second vectors including means for exchanging one portion of each vector by irreversible recombination(s) to generate recombinant final vectors after the recombination(s), wherein one of said vectors contains a gene of one of the two types and a gene of the other type, wherein the starting vectors respectively contain two attP lambda phage sites and two attB *E. coli* sites, arranged so as to allow two recombination events under the influence of an associated recombinase or integrase to form two sequences of stable attachment in each of the final vectors resulting from recombination, the two recombination sites in each of the starting vectors being in opposite orientation.

2. A method according to claim 1 wherein the genes of said first repertoire code for a population of variable regions of one of antibody light or heavy chains.

3. A method according to claim 1 wherein one of the two starting vectors further comprises a sequence coding for a recombinase or an integrase.

4. A method according to claim 1 wherein the final recombinant vector obtained from said starting vectors which contains the genes to be expressed is arranged so as to have a selection marker which is initially non-finctional and which is rendered finctional by recombination.

5. A method according to claim 1 wherein the final recombinant vector obtained from said starting vectors which contains the genes to be expressed is arranged so as to have a selection marker which is initially non-functional and which is rendered functional by recombination, said selection marker comprising a gene enabling selection when it is expressed and a promoter for the gene, the promoter being inserted in one of the starting vectors and the marker gene in the other.

6. A method according to claim 1 wherein the final recombinant vector obtained from said starting vectors which contains the genes to be expressed is arranged so as to have a selection marker which is initially non-functional and which is rendered functional by recombination, said selection marker comprising a gene enabling selection when it is expressed and a promoter for the gene, the promoter being inserted in one of the starting vectors and the marker gene in the other and the selection gene and its promoter being separated by an antiterminating sequence.

7. A method according to claim 1 wherein the final recombinant vector obtained from said starting vectors which contains the genes to be expressed is arranged so as to have a selection marker which is initially non-functional and which is rendered functional by recombination, said selection marker comprising a gene enabling selection when it is expressed and a promoter for the gene, the promoter being inserted in one of the starting vectors and the marker gene in the other and the selection gene and its promoter being separated by the NutL sequence.

8. A method according to claim 1 wherein the final recombinant vector obtained from said starting vectors which contains the genes to be expressed is arranged so as to have a selection marker which is initially non-functional and which is rendered functional by recombination, said selection marker being an antibiotic resistance gene with its promoter.

9. A method according to claim 1 wherein the final recombinant vector obtained from said starting vectors which contains the genes to be expressed is arranged so as to have a selection marker which is initially non-functional and which is rendered functional by recombination, said selection marker being an antibiotic resistance gene selected from the group consisting of genes resistant to tetracyclines, gentamycin, kanamycin and chloroamphenicol, with its promoter.

10. A method according to claim 1 wherein said starting vectors contain at least one phage and/or one plasmid origin of replication, said origins being arranged so that the final recombinant vectors contain only one phage and/or plasmid origin of replication.

11. A method according to claim 1 wherein said recombinant final vector containing a gene of one of the two types and a gene of the other type is a phagemid and one of the genes to be expressed is fused to a sequence coding for all or part of a polypeptide of the phage capsid.

12. A method according to claim 1 wherein said recombinant final vector containing a gene of one of the two types and a gene of the other type is a phagemid and one of the genes to be expressed is fused to a sequence coding for all or part of a polypeptide of the phage capsid, the fusion sequence consisting of the sequence of the gene coding for the III protein of the phage.

13. A method according to claim 1 wherein an inducible recombinase is used to control the recombination step between the starting vectors.

14. A method according to claim 1 wherein a thermoinducible recombinase is used to control the recombination step between the starting vectors.

15. Vectors obtained by the method of claim 1, containing a gene of one of the two types and a gene of the other type.

16. Vectors obtained by the method of claim 1 containing a gene of one of the two types and a gene of the other type, which are plasmid or phagemid type vectors.

17. Vectors obtainable by the method of claim 1, containing a gene of one of the two types and a gene of the other type.

18. Vectors obtainable by the method of claim 1 containing a gene of one of the two types and a gene of the other type, which are plasmid or phagemid type vectors.

19. Vectors obtained or obtainable by the method of claim 1, said vectors comprising a sequence coding for one of two types of polypeptides which can combine together and a sequence coding for the other of said two types, said sequences being accompanied in suitable frames by elements allowing their expression in a host, and said sequences being separated by stable attachment sequences.

20. Vectors obtained or obtainable by the method of claim 1, said vectors comprising a sequence coding for one of two types of polypeptides which can combine together and a sequence coding for the other of said two types, said sequences being accompanied in suitable frames by elements allowing their expression in a host, and said sequences being separated by stable attR and attL attachment sequences.

21. Vectors obtained or obtainable by the method of claim 1 containing a gene of one of the two types and a gene of the other type, one of said vectors comprising a functional sequence coding for a recombinase or integrase.

22. Vectors obtained or obtainable by the method of claim 1 containing a gene of one of the two types and a gene of the other type, said vectors comprising stable attachment sequences separated by a spacer.

23. Multicombinatorial libraries of vectors formed by vectors obtained or obtainable by the method of claim 1, combining in random fashion a sequence coding for one of the two types of polypeptides which can covalently or otherwise combine and a sequence coding for the other of said two types.

24. Multicombinatorial libraries of vectors formed by vectors obtained or obtainable by the method of claim 1 wherein the genes of said first repertoire code for a population of variable regions of one of antibody light or heavy chains, combining in random fashion a sequence coding for a variable portion of the antibody light chain and a sequence coding for a variable portion of the antibody heavy chain.

25. Vectors obtained or obtainable by the method of claim 2, said vectors comprising a sequence coding for a variable portion of the antibody light chain and a sequence coding for a variable portion of the antibody heavy chain, said sequences being accompanied in suitable frames by elements allowing their expression in a host, and said sequences being separated by stable attachment sequences.

* * * * *